United States Patent
Hayman

(10) Patent No.: US 8,464,718 B2
(45) Date of Patent: Jun. 18, 2013

(54) NECK FLANGE ATTACHMENT APPARATUSES FOR TRACHEOSTOMY TUBES

(75) Inventor: Sarah Hayman, Boulder, CO (US)

(73) Assignee: Covidien LP, Mansfield, MA (US)

( * ) Notice: Subject to any disclaimer, the term of this patent is extended or adjusted under 35 U.S.C. 154(b) by 197 days.

(21) Appl. No.: 13/028,968

(22) Filed: Feb. 16, 2011

(65) Prior Publication Data

US 2012/0204882 A1    Aug. 16, 2012

(51) Int. Cl.
  *A61M 16/00* (2006.01)
  *A62B 9/06* (2006.01)

(52) U.S. Cl.
  USPC ............................... 128/207.17; 128/207.14

(58) Field of Classification Search
  USPC ............. 128/200.26, 207.11, 207.14, 207.15, 128/207.17, 202.27; 24/593.1, 589.1; 403/59, 403/61, 116
  See application file for complete search history.

(56) References Cited

U.S. PATENT DOCUMENTS

| | | |
|---|---|---|
| 3,236,236 A | 2/1966 | Hudson |
| 3,655,612 A | 4/1972 | Stella |
| 3,824,999 A | 7/1974 | King |
| 3,973,569 A | 8/1976 | Sheridan et al. |
| 3,987,798 A | 10/1976 | McGinnis |
| 4,009,720 A | 3/1977 | Crandall |
| 4,033,353 A | 7/1977 | La Rosa |
| 4,068,658 A * | 1/1978 | Berman .................. 128/200.26 |
| 4,235,229 A | 11/1980 | Ranford et al. |
| 4,304,228 A | 12/1981 | Depel |
| 4,340,046 A | 7/1982 | Cox |
| 4,686,977 A | 8/1987 | Cosma |
| 4,852,565 A | 8/1989 | Eisele |
| 4,909,248 A | 3/1990 | McLennan Anderson |
| 5,054,482 A | 10/1991 | Bales |
| 5,056,515 A | 10/1991 | Abel |
| 5,067,496 A | 11/1991 | Eisele |
| 5,320,097 A * | 6/1994 | Clemens et al. ......... 128/207.17 |
| 5,361,754 A | 11/1994 | Stuart |
| 5,435,306 A | 7/1995 | Stuart |
| 5,458,139 A | 10/1995 | Pearl |
| 5,778,877 A | 7/1998 | Stuart |
| 5,819,734 A | 10/1998 | Deily et al. |
| 6,053,167 A | 4/2000 | Waldeck |
| 6,284,179 B1 | 9/2001 | Deily et al. |
| 7,086,402 B2 | 8/2006 | Peterson |
| 7,448,387 B2 | 11/2008 | Janatpour |
| 8,151,798 B2 * | 4/2012 | Thomas et al. .......... 128/207.29 |

(Continued)

FOREIGN PATENT DOCUMENTS

| | | |
|---|---|---|
| DE | 3819237 | 12/1988 |
| EP | 0037719 A1 | 4/1981 |

(Continued)

OTHER PUBLICATIONS

Tracoe medical GmbH-Products: Twist; Apr. 1, 2010; 34 pgs.

*Primary Examiner* — Kristen Matter

(57) ABSTRACT

Various embodiments of tracheostomy tube assemblies including a cannula and a flange are provided. One of the cannula and the flange includes a pair of slots and the other of the cannula and the flange includes a pair of protrusions adapted to be received by the pair of slots. The pair of slots and the pair of protrusions enable two or more degrees of freedom of movement of the flange with respect to the cannula.

18 Claims, 4 Drawing Sheets

U.S. PATENT DOCUMENTS

| | | | |
|---|---|---|---|
| 8,156,934 B2 * | 4/2012 | Trodler | 128/202.27 |
| 2003/0034036 A1 * | 2/2003 | Waldeck | 128/207.14 |
| 2005/0166924 A1 | 8/2005 | Thomas et al. | |
| 2006/0122036 A1 * | 6/2006 | Ferrara | 482/11 |
| 2007/0083262 A1 | 4/2007 | Matlock | |
| 2007/0255258 A1 | 11/2007 | Matlock et al. | |
| 2008/0149107 A1 * | 6/2008 | Byatt | 128/207.14 |
| 2008/0168986 A1 * | 7/2008 | Mythen | 128/200.26 |
| 2009/0229614 A1 | 9/2009 | Bateman | |
| 2009/0308397 A1 | 12/2009 | Neame | |
| 2010/0095968 A1 * | 4/2010 | Ogilvie et al. | 128/207.14 |
| 2010/0319705 A1 | 12/2010 | Thomas et al. | |
| 2011/0083672 A1 * | 4/2011 | Webster et al. | 128/207.15 |
| 2012/0048277 A1 * | 3/2012 | Waldron et al. | 128/207.14 |

FOREIGN PATENT DOCUMENTS

| | | |
|---|---|---|
| EP | 0107779 A1 | 4/1981 |
| EP | 0598948 A1 | 11/1992 |
| GB | 2007789 | 5/1979 |
| GB | 2205504 | 12/1988 |
| WO | 2008046418 A1 | 4/2008 |

* cited by examiner

NECK FLANGE ATTACHMENT APPARATUSES FOR TRACHEOSTOMY TUBES

BACKGROUND

The present disclosure relates generally to medical devices and, more particularly, to airway devices, such as tracheostomy tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air and medicaments into or out of a patient airway. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

More specifically, tracheal tubes may be used to control the flow of air or other gases through a patient's trachea. Such tracheal tubes may include endotracheal tubes or tracheostomy tubes. While patients may be intubated using endotracheal tubes during emergencies or shorter hospital stays, tracheostomy tubes are typically used for prolonged ventilation, as the use of a tracheostomy tube may be more comfortable for a patient.

A typical tracheostomy tube is generally inserted into the trachea via a surgical incision in the neck. After insertion of the tube into the trachea, a portion of the tracheostomy tube remains outside the patient. This portion extends outwards from the neck and may connect the tracheostomy tube to a ventilator or other medical device. Generally, this exterior portion of the tube is held in place by a flange that rests on the patient's neck and is further secured by straps to the patient. The inserted portion of the tracheostomy tube is generally mechanically coupled to the flange, typically by a snap or screw mechanism on the underside of the flange, which rests on the patient's neck. As such, the mechanical connection point typically provides for only a single degree of freedom of movement of the flange with respect to the inserted portion. Accordingly, during prolonged intubation periods, patient movement may not be accommodated by the tube and flange design, which cannot fully follow such movements. Certain devices attempt to address this problem by providing pillow or fabric protectors for the neck that may lift the flange slightly off the neck to avoid skin irritation, providing some additional comfort. However, these devices may be a less stable base for the tube at the patient's neck.

A stable attachment of the tracheostomy tube to the patient is advantageous insomuch as it reduces motion of the tube within the trachea. That is, because the exterior portion of the tracheostomy tube is connected to the inserted portion, when the exterior portion of the tube is shifted or moved, these movements may be translated to the interior portion of the tube. These movements may cause some discomfort for the patient if the tracheostomy tube shifts position within the trachea. Accordingly, there exists a need for tracheostomy tubes that reduce patient discomfort without translating patient movement to the interior portion of the inserted tracheostomy tube.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
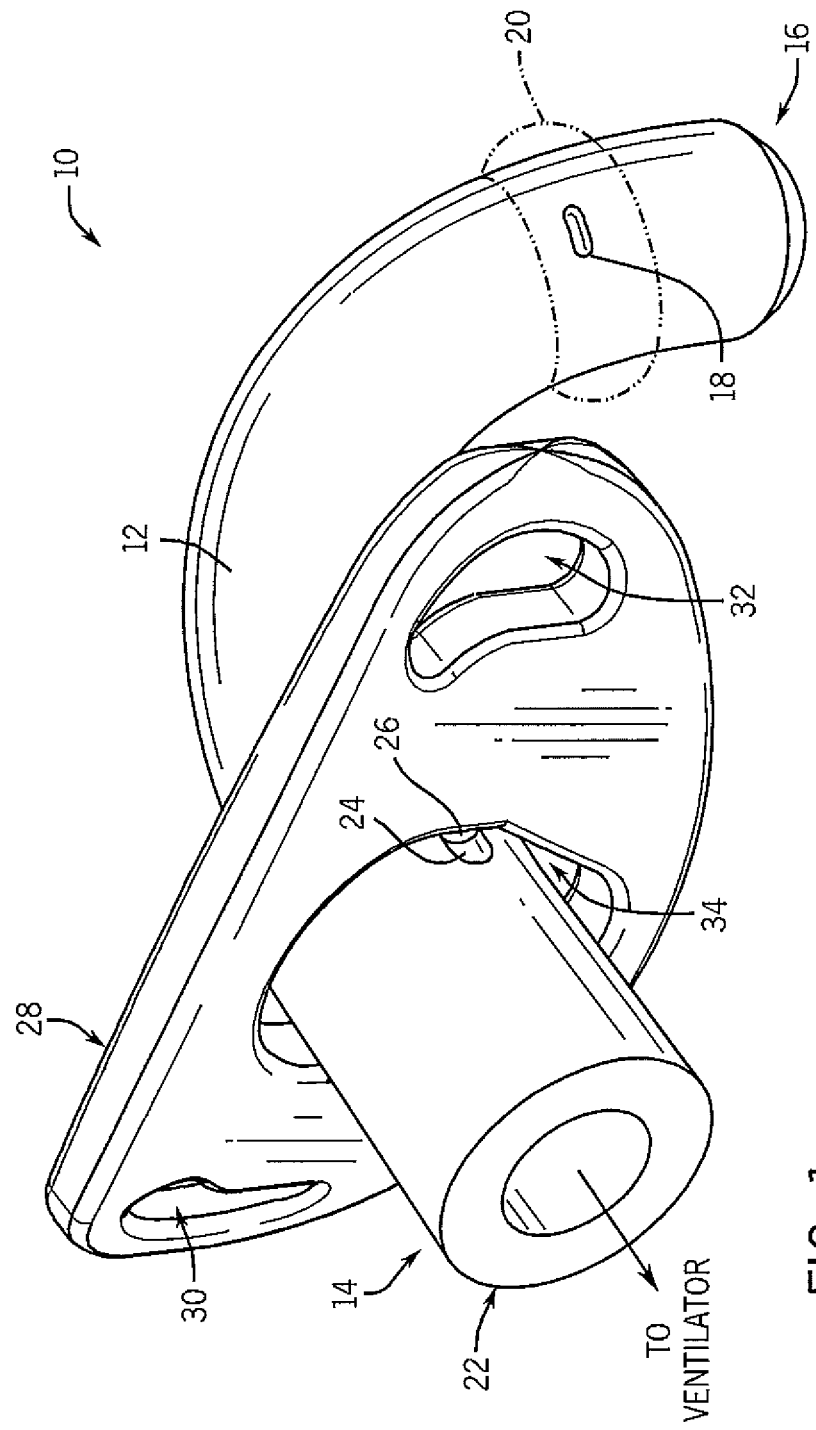
FIG. 1 is a perspective view of a tracheostomy tube assembly including a slot and a pin according to an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, provided herein are tracheostomy tube assemblies including a flange member and a cannula portion that are coupled together to provide two or more degrees of freedom of movement of the flange member with respect to the cannula. Such tube assemblies may allow for increased patient comfort during use. For example, by providing additional freedom of movement of the flange with respect to the cannula, presently disclosed tube assemblies may enable movement of the flange as the patient's neck moves without substantial displacement of the cannula. The foregoing feature may increase patient comfort since the movement of the flange member, which rests against the patient's neck, may more closely follow patient movement as compared to traditional designs.

Certain embodiments of the presently disclosed tracheostomy tube assemblies may include one or more features that facilitate the freedom of movement of the flange member with respect to the cannula. Specifically, in one embodiment, two elongated slots may be disposed in a proximal end of a cannula or in a collar coupled to the proximal end of the cannula. The elongated slots may be configured to receive pins or protrusions on the flange member and to enable movement of the pins and, thus, the flange member along the length of the elongated slots. Still further, in another embodiment, one or more slots may be provided on the flange member and one or more pins may be provided on the cannula to facilitate two or more degrees of freedom of movement of the flange member with respect to the cannula. Again, such physical features may enable the flange member to conform to the movement of the patient's neck during use without translating such movement to the cannula. That is, in certain embodiments, the tracheostomy tubes may include features that reduce the outside forces (e.g., those produced during movement of the patient's neck) that may be transferred to the inserted portion of the tube, which may cause discomfort if the tube shifts position and contacts the trachea.

The tracheostomy tube assemblies may be disposable rather than reusable and may be capable of conveying gas to and from the patient, such as during medical situations that necessitate prolonged ventilation. As such, the devices and techniques provided herein may enable maintaining a bidirectional gas flow between the patient and an external ventilation device. Accordingly, the tracheostomy tube assemblies provided herein may be adapted to be inserted into the trachea via a surgical incision in the neck such that after insertion of the tube into the trachea, a portion of tube remains outside the patient. This portion extends outwards from the neck and may connect the tracheostomy tube to a ventilator or other medical device. That is, the provided tracheostomy tube assemblies may be used in conjunction with auxiliary devices, such as airway accessories, ventilators, humidifiers, and so forth, which may cooperate with the tube assemblies to maintain airflow to and from the lungs of the patient. For example, the tracheal tubes may be coupled to an adapter or connector that is configured to couple the tracheostomy tube assemblies described herein to the desired auxiliary device.

FIG. 1 is a perspective view of an exemplary tracheostomy tube assembly 10 according to an embodiment. In the depicted embodiment, the tracheostomy tube assembly 10 includes an arcuate cannula 12 having a proximal end 14 and a distal end 16, which is generally sized and configured to be inserted into a patient's neck through a surgical incision for prolonged ventilation. When the tracheostomy tube assembly 10 is in use, the distal end 16 as well as the major portion of the length of the cannula 12 will reside within the trachea, with the proximal end 14 being generally flush with the anterior surface of the patient's neck. The cannula 12 may also feature a small lumen (not shown) within the wall, terminating in notch 18 that may be used to fill a balloon type sealing cuff 20 at the patient insertion end. In some embodiments, the cuff 20 may be a urethane balloon bonded to the exterior of the cannula 12 such that the notch 18 is encompassed. The cuff 20 may be inflated within the patient's airway to provide an additional seal in some embodiments.

In some embodiments, the cannula 12 may also include a suction lumen (not shown in FIG. 1) that extends from a location on the proximal end 14 of the cannula 12 positioned outside the body when in use to a location around the cuff 20 inside the body. The suction lumen may terminate in a port through which secretions accumulated around the cuff may be aspirated. For example, a port may be located above the cuff 20 or one or more ports may be located anywhere along the length of the cannula 12 such that they aspirate secretions from the airway of the patient. Further, in some embodiments, an exterior suction tube may connect to the suction lumen for the removal of the suctioned fluids, for example, via a vacuum connected to the exterior suction tube.

In the illustrated embodiment, the tracheostomy tube assembly 10 includes a collar 22 that is substantially in line with the proximal end 14 of the cannula 12. The collar 22 may be adapted to directly or indirectly connect the tracheostomy tube assembly 10 to any suitable medical device. For example, in dual cannula tracheostomy tubes, the collar 22 may serve as an insertion point for a disposable cannula lining or may be suitably sized and shaped to connect the tracheostomy tube assembly 10 via medical tubing, suitable connectors, or other devices to a mechanical ventilator.

In one embodiment, the collar 22 may be overmolded onto the cannula 12 during manufacturing of the assembly 10 such that the cannula 12 and the collar 22 form a single integral unit. As illustrated, the collar 22 portion of the cannula 12 includes a slot 24 disposed therein on a first side of the collar 22 and another slot disposed on a second side of the collar 22 (not shown in FIG. 1). The slot 24 may be configured to receive a spherical pin 26 of a flange 28 connected to the proximal end 14 of the cannula 12 when the proximal end 14 of the cannula 12 is received through an aperture 34 of the flange 28. The flange 28 is adapted to rest on the neck of the patient during use and may feature openings 30 and 32 designed to accommodate attachment straps that may further secure the tracheostomy tube assembly 10 to the patient's neck.

The slot and pin arrangement illustrated in FIG. 1 may enable two or more degrees of freedom of movement of the flange 28 with respect to the cannula 12 when the tracheostomy tube assembly 10 is in use. That is, structural features of embodiments of the present invention may enable the flange 28 to pivot, slide, and otherwise move to accommodate outside forces, such as those generated by movement of the patient's neck. For example, if the patient exerts a force on the flange 28 via neck movement, the flange 28 may transmit some of that force into movement of the flange 28 (e.g., when the pin 26 moves within the slot 24) such that the portion of the cannula 12 disposed inside the patient's trachea does not experience the full force exerted on the flange 28. As such, movement of the cannula 12 may be reduced, which may result in enhanced patient comfort as compared to traditional tracheostomy assemblies that provide limited freedom of movement of the flange with respect to the cannula.

Figure 2:
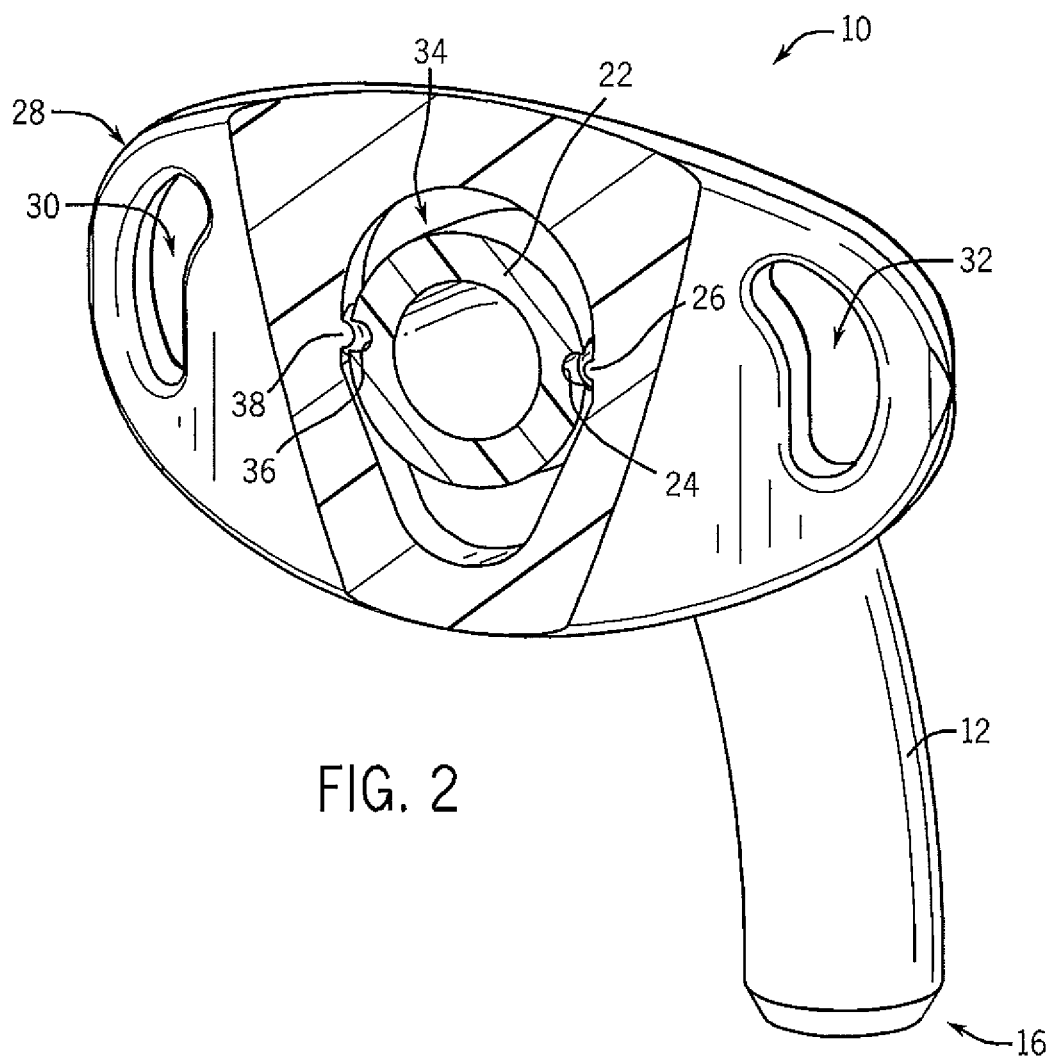
FIG. 2 is a sectional view of the tracheostomy tube assembly embodiment of FIG. 1 illustrating the slot and spherical pin arrangement in more detail.

FIG. 2 is a sectional view of the tracheostomy tube assembly 10 of FIG. 1 illustrating the slot and pin arrangement in more detail. As shown, the slot 24 is disposed on a first side of the collar 22, and a second slot 36 is disposed on a second side of the collar 22 opposite the first side. The spherical pin 26 of the flange 28 is disposed in the slot 24 and is configured to move within the limits of the slot 24 to accommodate external forces. Similarly, a second spherical pin 38 is received by the second slot 36 that facilitates movement of the second side of the flange 28 with respect to the cannula 12. Features of the spherical pins 26 and 38 and the slots 24 and 36 configured to receive such pins are discussed in more detail below with respect to FIGS. 3-9. It should be noted that the particular configuration of the pins and slots, while presently contemplated, may be varied in particular designs.

Figure 3:
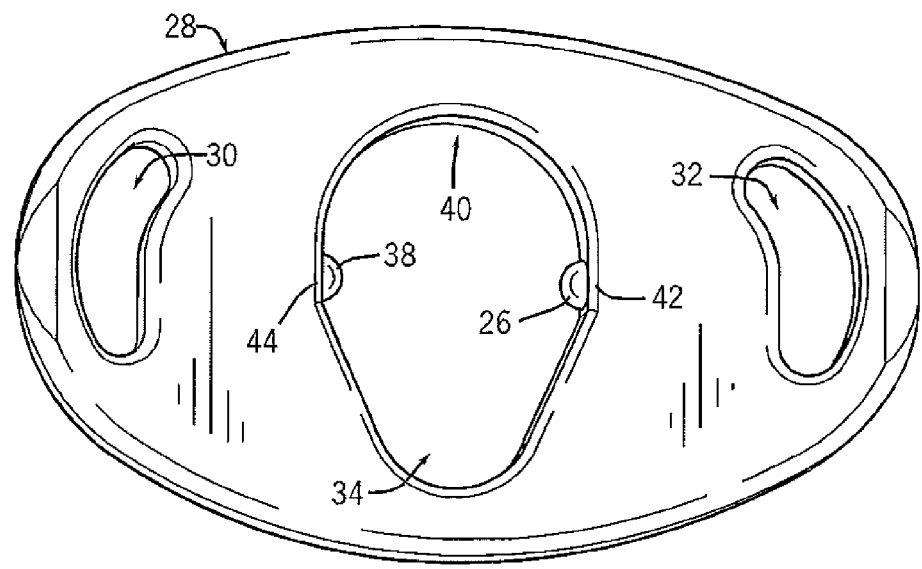
FIG. 3 illustrates a perspective view of a flange of the tracheostomy tube assembly embodiment of FIG. 1 showing features of the flange in more detail.

Specifically, FIG. 3 illustrates a perspective view of the flange 28 showing features of the flange 28 in more detail. As shown, the flange 28 includes the openings 30 and 32 that are configured to receive straps for attachment of the flange 28 to the patient's neck. The flange 28 further includes the aperture 34 defined by circumferential wall 40 that is sized and configured to receive a cannula, for example, during manufacturing of the tracheostomy tube assembly. The illustrated flange 28 includes the first spherical pin 26 that extends outward into the aperture 34 from a first surface 42 of the circumferential wall 40. The second spherical pin 38 also extends outward into the aperture 34 but from a second surface 44 of the circumferential wall 40 opposite the first surface 42. As such, the first spherical pin 26 and the second spherical pin 38 oppose one another from opposite sides of the opening of the flange 28 such that each spherical pin is configured to engage a separate slot when coupled to a suitable cannula.

In some embodiments, during manufacturing, the illustrated flange 28 may be formed from one or more suitable materials by any desired process. For example, in one embodiment, an inner shell of the flange 28 with the pins 26 and 38 may be composed of a rigid thermoplastic material (e.g. polyvinyl chloride (PVC)) and overmolded with a flexible thermoplastic material (e.g., PVC). Accordingly, in certain embodiments, the pins 26 and 38 may be made of a rigid material, such as PVC. Such a manufacturing process may endow the flange 28 with flexibility and strength as desired for the given application. For example, in such embodiments, the flexible overmolded material may be provided to increase patient comfort since the flange 28 contacts the neck of the patient during use. However, the rigidity of the pins and the core of the flange may endow the flange with the desired strength. However, in other embodiments, the flange 28 may be formed in any desired way from any of a variety of suitable materials, as would be understood by one skilled in the art.

Figure 4:
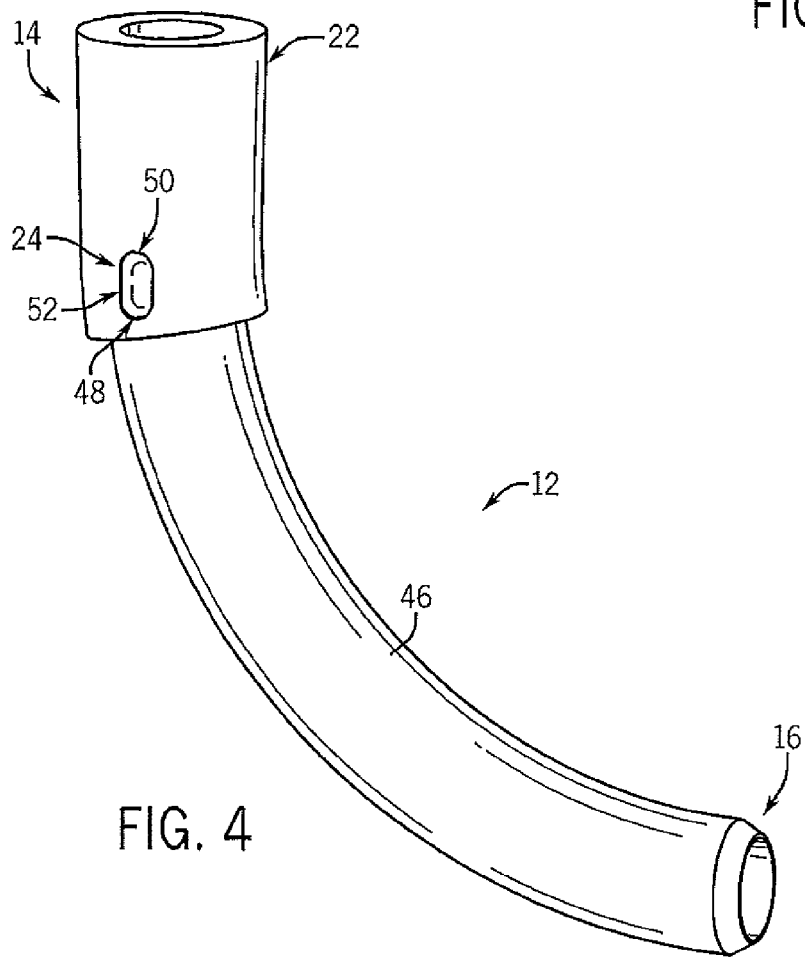
FIG. 4 illustrates a perspective view of a cannula of the tracheostomy tube assembly embodiment of FIG. 1.

FIG. 4 is a perspective view of the cannula 12 of FIG. 1 in accordance with an embodiment. As shown, the cannula 12 includes a tubular portion 46 and the collar 22. The collar 22 includes the slot 24 disposed therein. In the illustrated embodiment, the slot 24 is a shaped as an elongated with a first end 48 and a second end 50 disposed about a middle elongated portion 52. During use, the pins 26 and 38 are configured to slide within the elongated slot 24, for example, from spherical end 48 to end 50 through middle portion 52. As such, in some embodiments, the slot 24 is configured to allow freedom of movement of a pin throughout operation. That is, in some embodiments, the spherical pin disposed in the slot 24 may not be configured to lock into place, but rather is free to move in accordance with one or more external forces exerted thereon during use. In certain embodiments, if desired, one or more coatings may be applied to the slot 24 to facilitate such freedom of movement and to substantially reduce friction between the pin and the slot during movement.

The cannula 12 may be formed via any desirable process from any of a number of suitable materials. For example, in one embodiment, the tubular portion 46 of the cannula may be injection molded to endow the portion 46 with the desired rigidity. Further, the collar 22 may be overmolded onto the tubular portion 46 to form an integral cannula 12. However, as before, a variety of other suitable methods and materials may be utilized to form a suitable cannula having a slot in accordance with certain embodiments.

FIGS. 5-9 illustrate exemplary slots that may be disposed on the cannula or the flange. That is, as illustrated in FIGS. 1-4, the slots may be located on the cannula, and the pins may be located on the flange. However, in other embodiments, the slots may be located on the flange, and the pins may be located on any suitable portion of the cannula. As such, presently contemplated embodiments are not limited to placement of the slots described below on the cannula.

Figure 5:
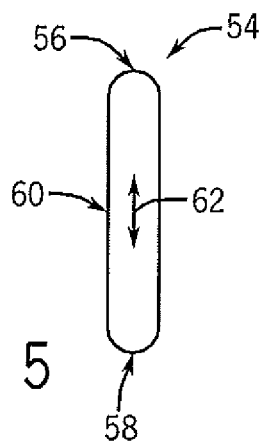
FIG. 5 is a schematic illustrating an embodiment of a vertically disposed elongated slot that may be disposed on a portion of an exemplary tracheostomy tube assembly.
Figure 6:
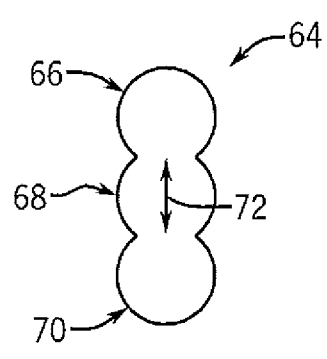
FIG. 6 is a schematic illustrating an embodiment of a spherical elongated slot that may be disposed on a portion of an exemplary tracheostomy tube assembly.

Turning now to the embodiment of FIG. 5, an exemplary elongated spherical slot 54 is shown. The slot 54 includes a first spherical end 56 and a second spherical end 58 as well as an elongated middle portion 60. During use, a pin received therein is enabled to fluidly move between the ends 56 and 58, as illustrated by arrow 62. That is, in the embodiment of FIG. 5, continuous motion of the pin is enabled throughout the slot 54 as dictated by one or more external forces. However, in the embodiment of FIG. 6, an elongated slot 64 includes a first portion 66, a second portion 68, and a third portion 70, which are each configured to receive the pin as the pin moves in the direction indicated by arrow 72.

Figure 7:
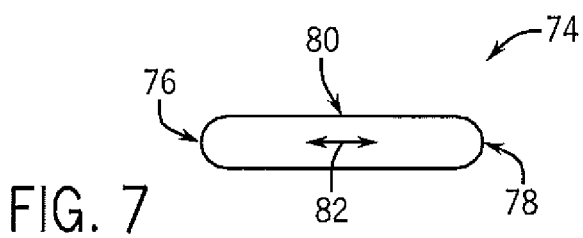
FIG. 7 is a schematic illustrating an embodiment of a horizontally disposed elongated slot that may be disposed on a portion of an exemplary tracheostomy tube assembly.

FIG. 7 illustrates a horizontally disposed elongated slot 74 rotated approximately 90° as compared to the slot 54 of FIG. 5. As before, the slot 74 includes a first portion 76, a second portion 78, and a middle portion 80 through which a pin may move in a horizontal direction, as shown by arrow 82. As such, certain embodiments may enable movement of a pin in a vertical or horizontal direction, as dictated by the slot disposed in one of the cannula or the flange. Further, in other embodiments, the slot may be oriented at any desired angle between 0°, as defined by the slot 54 of FIG. 5, and 90°, as defined by the slot 74 of FIG. 7.

Figure 8:
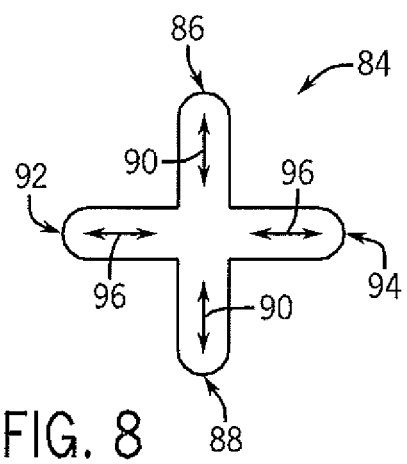
FIG. 8 is a schematic illustrating an embodiment of a slot that may be disposed on a portion of an exemplary tracheostomy tube assembly to enable horizontal and vertical movement of a spherical pin in accordance with an embodiment.

FIG. 8 illustrates another embodiment of an exemplary slot 84 configured to allow both horizontal and vertical movement of a pin disposed therein. The slot 84 includes a first end 86 and a second end 88 that define a longitudinal path of movement through which a pin may move, as shown by arrows 90. Further, the slot 84 also include a third end 92 and a fourth end 94 that define a horizontal path of movement through which a pin may move in the directions indicated by arrows 96. As such, in this embodiment, freedom of movement of the pins is provided in both a horizontal as well as a vertical direction.

Figure 9:
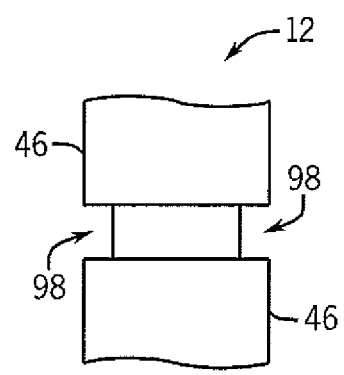
FIG. 9 is a schematic illustrating an embodiment of an annular recess that may be disposed on an embodiment of a cannula portion of an exemplary tracheostomy tube assembly.

FIG. 9 illustrates an embodiment including an annular recess 98 disposed in the tubular portion 46 of the cannula 12. That is, in this embodiment, a single slot extends about the circumference of the tubular portion 46 of the cannula 12 in the form of annular recess 98. In such an embodiment, the annular recess 98 may be suitably configured to accommodate one or more pins to enable fluid movement of the flange with respect to the cannula during use.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheostomy tube assembly, comprising:
   a cannula comprising a distal end and a proximal end, the distal end being adapted to be inserted into a patient's trachea and the proximal end comprising a collar comprising a first slot and a second slot; and
   a flange member comprising an aperture configured to receive the proximal end of the cannula, a first protrusion adapted to be received by the first slot, and a second protrusion adapted to be received by the second slot, wherein the first protrusion and the second protrusion extend into the aperture from opposite surfaces of the flange member, wherein the first protrusion and the second protrusion of the flange member are configured to engage with the first slot and the second slot of the cannula to enable the flange member to move with two or more degrees of freedom with respect to the cannula when the tracheostomy tube assembly is positioned for operation such that the distal end of the cannula is inserted into the patient's trachea and the flange member is engaged with the patient's neck to support the tracheostomy tube assembly and maintain the flange member outside of the patient's body, wherein one of the two or more degrees of freedom of movement comprises movement of the flange member longitudinally with respect to the length of the cannula between the distal end and the proximal end of the cannula.

2. The tracheostomy tube assembly of claim 1, wherein the first slot or the second slot comprise an elongated shape extending longitudinally from the proximal end toward the distal end of the cannula.

3. The tracheostomy tube assembly of claim 1, wherein the first slot or the second slot comprise an elongated spherical shape.

4. The tracheostomy tube assembly of claim 3, wherein the first slot or the second slot comprise an annular recess extending at least partially around the circumference of the cannula.

5. The tracheostomy tube assembly of claim 1, wherein the first protrusion and the second protrusion comprise a rigid thermoplastic polymer integral with a rigid thermoplastic shell of the flange member, and wherein the flange member comprises a flexible thermoplastic polymer overmolded over the rigid thermoplastic shell.

6. The tracheostomy tube assembly of claim 1, wherein the cannula comprises an injection molded tubular portion onto which the collar is overmolded.

7. A tracheostomy tube assembly, comprising:
a cannula comprising a distal end and a proximal end, the distal end being adapted to be inserted into a patient's trachea and the proximal end comprising one of a pair of slots or a pair of pins; and
a flange member comprising the other of the pair of slots configured to engage with the pair of pins on the cannula, or the pair of pins configured to engage with the pair of slots on the cannula, and wherein when the tracheostomy tube assembly is positioned for operation such that the distal end of the cannula is inserted into the patient's trachea and the flange member supports the tracheostomy tube assembly via engagement with the patient's neck to maintain the flange member outside of the patient's body, the pair of slots and the pair of pins are configured to enable two or more degrees of freedom of movement of the flange member with respect to the body, wherein one of the two or more degrees of freedom of movement comprises movement of the flange member longitudinally with respect to the length of the cannula between the distal end and the proximal end of the cannula.

8. The tracheostomy tube assembly of claim 7, wherein the pair of slots comprise a pair of longitudinally disposed slots disposed in a portion of the cannula and extending from the proximal end of the cannula toward the distal end of the cannula.

9. The tracheostomy tube assembly of claim 8, wherein the pair of pins is integral with the flange member and the pins extend from opposite surfaces of the flange member, and engage with the slots disposed on the cannula.

10. The tracheostomy tube assembly of claim 7, wherein the flange member comprises an opening configured to receive the cannula and defined by a circumferential wall of the flange member, and wherein the pair of slots is disposed in the circumferential wall such that the slots are disposed on opposite sides of the opening.

11. The tracheostomy tube assembly of claim 10, wherein the pair of pins are disposed on the proximal end of the cannula, wherein each pin of the pair of pins is circumferentially displaced from the other pin at substantially the same radial position about the cannula.

12. The tracheostomy tube assembly of claim 7, wherein one of the two or more degrees of freedom of movement comprises pivotal movement of the flange member with respect to the cannula.

13. The tracheostomy tube assembly of claim 7, wherein the cannula comprises a collar integrally formed therewith, and wherein the collar comprises the one of the pair of slots or the pair of spherical pins.

14. A tracheostomy assembly, comprising:
a cannula comprising a distal end and a proximal end, the distal end being adapted to be inserted into a patient's trachea;
a collar coupled to the proximal end of the cannula; and
a flange coupled directly to the collar or the cannula and comprising a pivoting means that permits pivotal movement about a transverse axis in two or more degrees of freedom of movement of the flange with respect to the collar or the cannula when the tracheostomy tube assembly is positioned for operation such that the distal end of the cannula is inserted into the patient's trachea and the flange member is engaged with the patient's neck to support the tracheostomy tube assembly and maintain the flange member outside of the patient's body, wherein one of the two or more degrees of freedom of movement comprises movement of the flange member longitudinally with respect to the length of the cannula between the distal end and the proximal end of the cannula.

15. The tracheostomy assembly of claim 14, wherein the cannula or the collar comprises a pair of slots.

16. The tracheostomy assembly of claim 15, wherein the pivoting means comprises a pair of protrusions configured to be received by the pair of slots to permit the pivotal movement of the flange with respect to the collar or the cannula.

17. The tracheostomy assembly of claim 15, wherein each slot of the pair of slots comprises an elongated shape positioned between 0° and 90° with respect to an axial plane of the collar or the cannula.

18. The tracheostomy assembly of claim 14, wherein the pivoting means of the flange comprises a pair of slots configured to engage with a pair of protrusions disposed on the collar or the cannula.

* * * * *